(12) United States Patent
Steigerwald et al.

(10) Patent No.: US 7,763,241 B2
(45) Date of Patent: Jul. 27, 2010

(54) HAIR DYEING COMPOSITION AND METHOD

(75) Inventors: Sean Steigerwald, Stamford, CT (US); Freda E. Robinson, Nyack, NY (US); Kenneth A. Buckridge, Fort Lee, NJ (US)

(73) Assignee: Avon Products, Inc., New York, NY (US)

( * ) Notice: Subject to any disclaimer, the term of this patent is extended or adjusted under 35 U.S.C. 154(b) by 1245 days.

(21) Appl. No.: 11/322,093

(22) Filed: Dec. 29, 2005

(65) Prior Publication Data

US 2007/0151047 A1    Jul. 5, 2007

(51) Int. Cl.
*A61Q 5/06* (2006.01)
*A61Q 5/00* (2006.01)
*A61Q 1/10* (2006.01)

(52) U.S. Cl. .................... 424/70.6; 424/70.1; 424/70.7; 424/401

(58) Field of Classification Search ............ 8/404; 424/70.1
See application file for complete search history.

(56) References Cited

U.S. PATENT DOCUMENTS 6,328,950 B1    12/2001   Franzke et al.
6,908,491 B2    6/2005    Fischer et al.
2004/0076595 A1 *  4/2004   Khan ............... 424/70.11

FOREIGN PATENT DOCUMENTS

| GB | 2149806 A | * | 6/1985 |
| JP | 60-87210 | * | 5/1985 |
| JP | 11-139820 |   | 5/1999 |
| JP | 11-139946 |   | 5/1999 |
| JP | 2003-095898 | * | 4/2003 |

OTHER PUBLICATIONS

Hata, M., "Hair-Coloring Matter", Apr. 3, 2003, JP 2003-095898. machine translation.*
Nakamura, Y., "Hiar dye Composition", May 16, 1985, JP360087210A, abstract.*

* cited by examiner

*Primary Examiner*—Gina C Yu
(74) *Attorney, Agent, or Firm*—Charles J Zeller; Joan M. McGillycuddy; Anthony M. Santini

(57) ABSTRACT

Hair coloring compositions and methods of coloring hair with such compositions for providing a temporary color to the hair are disclosed, which compositions comprise an inorganic colored pigment preferably selected from the group consisting of iron oxides, ultramarines, and mixtures thereof, a non-volatile dimethicone copolyol, and preferably a cationic deposition aid.

24 Claims, No Drawings

HAIR DYEING COMPOSITION AND METHOD

FIELD OF INVENTION

The present invention relates to the dyeing of hair. In particular the invention concerns compositions and methods for dyeing hair with a pigment, especially a pigment selected from the group consisting of iron oxides, ultramarines, and mixtures thereof.

STATE OF THE ART

The use of pigments to dye hair has not achieved great success because the compositions containing the pigment colorant are not water fast. That is, the color imparted to the hair is easily removed, and typically is removed by rinsing of the hair with water. Thus, the application of the composition to the hair followed by rinsing of excess composition from the hair results in the removal of the color. One prior art pigment-containing hair color composition is described in British patent No.2,149,806, which describes hair coloring compositions containing mica, iron oxides, and methylphenylpolysiloxane. Published Japanese No.11-139,820 describes hair coloring compositions using a colored mica obtained by forming a 400-800 nm titanium dioxide layer on the surface of the mica and further coating this composite with a dye or pigment, for example with red iron oxide. Published Japanese No. 11-139946 discloses hair dyeing compositions comprising 1.0 to 20% of an α-hydroxy carboxylic acid and 0.5 to 10% by weight of the titanium dioxide-containing colored mica of the JP '820 application. U.S. Pat. No. 6,328,950 describes temporarily coloring hair with an aerosol foam of a hair-fixing polymer, one gel forming thickener, and at least one inorganic pigment. Also known in the art the so called hair mascaras. These are products that contain inorganic pigments in a composition of paste-like consistency, which are intended for application to hair. The hair mascaras lack substantivity and are removable by rinsing with water.

OBJECTS OF THE INVENTION

It is an object of the invention to provide a temporary hair coloring composition.

It is another object of the invention to provide a method temporary dyeing hair.

It is another object of the invention to provide a temporary hair coloring composition that uses inorganic pigments to impart a color to the hair.

Yet another object of the invention is to provide a method for providing substantivity of inorganic pigments to hair.

These and other objects and advantages of the invention will become obvious from the following detailed descriptions.

SUMMARY OF THE INVENTION

The temporary hair coloring compositions of the invention comprise an inorganic pigment. The pigment is preferably at least one selected from the group consisting of iron oxides, ultramarines, and mixtures thereof. The pigments are present in an amount effective for imparting a color to hair. Typically, the pigment is present in an amount of from about 0.1 to about 15% by weight of the total composition. The compositions further comprise a nonvolatile dimethicone copolyol. When applied to hair fibers, the dimethicone copolyol provides a coating on the hair that is substantive to the hair. The inorganic pigment is dispersed in the coating on the hair to provide coloration to the hair. The dimethicone copolyol is present in an amount to coat the hair. The compositions of the invention further comprise a cosmetically acceptable vehicle. In another aspect of the invention, the compositions preferably further comprise a cationic deposition aid to enhance the substantivity of the inorganic pigments to the hair. The cationic deposition aid is typically present in an amount of from about 0.01 to about 10% by weight of the total composition.

The invention also concerns a method of dyeing hair by imparting to the hair a coloration obtained by distributing an inorganic pigment on the surface of the hair. The method comprises applying to the hair a hair dyeing composition comprising at least one inorganic pigment, a dimethicone copolyol, and a cosmetically acceptable vehicle, and rinsing excess hair dyeing composition from the hair. In another aspect of the invention the method further includes applying a composition containing an inorganic pigment, a nonvolatile dimethicone copolyol, a cationic deposition aid, and a cosmetically acceptable vehicle.

DETAILED DESCRIPTION OF THE INVENTION

Although cosmetic composition containing an inorganic pigment, such as hair mascaras, to impart color to skin, lips and eyelashes are known, compositions to temporarily color hair on the head of a consumer have not met with success because the pigment washes right off the hair. Such hair coloring products should also leave the hair soft and manageable, and should provide natural movement of the hair, especially longer hair, over three inches, especially longer than six inches. By hair is meant hair on the head of the consumer, i.e., facial hair and especially scalp hair, and does not include keratinous fibers elsewhere on the body of the consumer.

It has been found that compositions containing an inorganic pigment together with a nonvolatile dimethicone copolyol in a cosmetically acceptable vehicle impart a coloration to the hair that is resistant to removal by water rinsing. Such water rinse is a necessary step in the method of dyeing hair with an inorganic pigment since it is necessary to remove excess composition from the hair before drying the hair. While not wishing to be bound by any theory of how the invention works, it is believed that the nonvolatile copolyol when applied to hair fibers forms a substantive film on the hair fibers, with the particles of pigment within that substantive coating.

It has been found that the substantivity is greater when the composition containing the pigment and the dimethicone copolyol is applied to damaged hair. Thus, the intensity of the color imparted to hair is greater when the composition is applied to damaged hair, and the degree of water fastness is greater as well. It has been found that incorporating a cationic deposition aid enhances the substantivity of the coating, and thus provides even greater resistance to removal by water rinsing. The incorporation of the cationic deposition aid thus improves the intensity of the color imparted to the hair and also improves the water fastness of the hair coloration. The compositions of the invention provide a hair coloring that also resists transfer from the hair to clothing or from the hair to skin. The composition may be used as a coloring treatment or as a highlighting treatment and is non-damaging and less irritating than typical hair coloring products that use chemical dyes that penetrate the hair or that react inside the hair shaft. The treatment can be a one-time treatment or used on a regular basis for a continuous color treatment.

The compositions are applied to the hair by intimately contacting the hair fibers, preferably from root to tip. While it is preferred to have the hair damp, it can be treated dry. Especially when dyeing damaged hair, the color imparted to the hair may build-up over the course of periodic applications of the composition, which deepens the intensity of the color. This can occur in the absence of intervening shampooings or even when the composition is applied periodically with intervening shampooing. This accumulation of color beneficially maintains and deepens color, enhances gray coverage, improves shine, and reduces or does away with other color treatments that may be more irritating. Nonetheless, the color is generally removable within one to three shampooings, more usually within two shampooings, and accordingly is considered to be a temporary hair color.

The compositions of the invention are especially suitable to provide a temporary color to the hair where it is intended to be removed within a day or two. The compositions and methods are ideally suited for those individuals who wish to augment their own natural color and is also suitable to provide color highlights to hair if applied by streaking the composition in the hair. The composition can be used to deposit color on damaged, virgin or grey hair.

The compositions of the invention give the hair a nice, smooth feel when the hair is wet or dry as compared to mascara treated hair. The hair is more manageable, has more shine, and there is no tacky feel.

Unless otherwise indicated, all percents in the specification and claims are by weight based on the total weight of the composition, on an actives basis.

The Inorganic Pigments The colorants used in the present invention are colored inorganic pigments, natural or synthetic. Thus, mineral such as $TiO_2$ and mica are not colored inorganic pigments for use in accordance with this invention to provide a coloration to the hair. The pigments typically have a particle size of from about 0.03 to about 50μ, preferably from about 0.5 to about 10μ, and most preferably from about 1 to about 5μ. Suitable inorganic pigments include iron oxide, chromium oxide green, ferric blue, carbon black, manganese violet, ultramarines, and combinations thereof. The iron oxides occur as black iron oxide, yellow iron oxide, and red iron oxide, and can be blended to give brown, reddish and blond tones depending on the color of the hair being dyed. Brown iron oxide is a blend of the red, yellow and black iron oxides. Ultramarines are blue, green, pink, red, and violet synthetic sodium aluminum sulfosilicates. Iron oxides and ultramarines are preferred with iron oxides most preferred. Iron oxides are commercially available from Sun Chemical Co. (C33-134 Black, C33-128 Russet, C33-8073 Yellow, Cosmetic brown C33-115); Hilton Davis (34-3068 Pure Oxy Black, 3551 Red, 34-3170 Yellow), Color Techniques Inc (A-1404 Black, A1301 Yellow); LCW (C7080 Red); and Warner-Jenkinson Co. (Cosmetic Yellow Oxide 3506S). Ultramarines are commercially available from Hilton Davis (Blue 10-34-PC-3516, Violet 10-34-PC-3514); LCW (Bleu D'Outremer W 6806, Violet D'Outremer W 782); and Warner-Jenkinson Co. (C7106 Blue, C7102 Violet)

The pigments used in the compositions and methods herein may be encapsulated. Suitable encapsulants are polysaccharides such as cellulose and cellulose derivatives such as hydroxyethyl cellulose, hydroxypropyl cellulose, and hydroxypropyl methyl cellulose, pectin and its derivatives, sugars such as mannitol and sorbitol and derivatives of sugars, natural and synthetic gums and resins such as guar gum, alginates, carrageenan, xanthan gum, gelatin, and rosin. Mention may also be made of chitin and its derivatives. These encapsulants are preferably water soluble, so that they release the enclosed inorganic pigment when used by application to hair that is wet or is being wetted. Examples of encapsulated pigments suitable for use in the present invention are Red Unispheres P018.1935 sold by Induchem. It should further be noted that coated pigments, that is, pigments coated with silica or other mineral materials, for example using the Sol-Gel process are not suitable in the compositions of the present invention. If the pigment is encapsulated, the encapsulates are broken as the composition is worked on the hair from root to tip. Preferably the pigments are used in their free form.

The pigments are present in the compositions in an amount effective to dye hair, and typically from about 0.1 to about 15%, preferably from about 0.5 to about 10%, most preferably from about 1 to about 5% by weight of the total composition.

The Dimethicone Copolyol Component

The compositions also contain a dimethicone copolyol, which is an ethoxylated and/or propoxylated copolymer of polydimethylsiloxane and methylsilicone. The dimethicone copolyols suitable in the present invention are those that are able to provide a substantive coating on the hair fiber and also to deposit the inorganic pigment on the hair fiber. The dimethicone copolyols thus are nonvolatile. As used herein the term "nonvolatile" means that the dimethicone copolyol has a vapor pressure of less than 2 mm of mercury at 20° C. The dimethicone copolyols are generally provided as a mixture of the copolyol in a volatile cyclomethicone solvent or dispersant. The vapor pressure referred to above is for the copolyol, and does not include the volatile dispersant, which evaporates rapidly when applied to the hair and does not participate in the coating of the hair.

Suitable dimethicone copolyols are those that have from 1 to 30 moles of ethylene oxide and 10 to 50 moles of propylene oxide, and preferably 10 to 25 moles ethylene oxide and 15 to 30 moles propylene oxide. Examples are PEG/PPG-18/18 dimethicone (sold as Dow Corning 190 surfactants), PEG/PPG-15/15 dimethicone (sold as Dow Corning 5330 fluid), and PEG/PPG-20/23 dimethicone (sold as OSI Silsoft 430). A preferred example is PEG/PPG 20/15 dimethicone (GE SF 1528), which is the alkoxylated derivative of dimethicone containing an average of 20 moles of ethylene oxide and 15 moles of propylene oxide. Other examples of said emulsifiers are PEG/PPG 19/19 dimethicone, and lauryl PEG/PPG 18/18 methicone.

The dimethicone copolyol may be obtained and used as a 100% active material, but is preferably provided in a cyclomethicone solvent or dispersant for ease of use. The dimethicone copolyol material as received from the vendor can be modified as convenient by the addition of more cyclomethicone. Typically, as used in formulating the compositions of the invention, the weight ratio of the dimethicone copolyol to the cyclomethicone may vary from 95:5 to 5:95. A commercially available dimethicone coplyol is GE SF 1528, which is an 8% by weight active PEG/PPG 20/15 dimethicone in a 92% by weight cyclomethicone pentamer base.

The amount of dimethicone copolyol present in the compositions of the present invention is typically from about 0.01 to 10%, preferably from about 0.05 to about 2.5%, and most preferably from about 0.1 to about 1.5% by weight of the total composition. While higher levels are not excluded, such higher levels do not marginally improve deposition of color.

The Cationic Deposition Aid

Hair typically has an anionic character with a net negative charge. Accordingly, a cationic deposition aid with a net positive charge will substantially neutralize the prevailing anionic character of the hair. It has been found that by neutralizing the anionic character of the hair, the compositions of the present invention containing the inorganic pigments and the dimethicone copolyol provide better color deposition than without such neutralization. Accordingly in a preferred aspect of the invention the compositions of the invention further comprise a cationic deposition aid. The deposition aid also provides conditioning and manageability to the hair.

Suitable cationic deposition aids include monoalkyl, dialkyl or polyalkyl quaternary ammonium compounds. Among the suitable quaternary ammonium compounds are those of the general formula

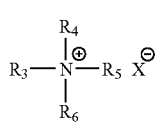

I wherein:
$R_3$ (i) is a saturated or unsaturated, branched or nonbranched alkyl with 8 to 22 carbon atoms; (ii) has the structure $R_7CONH(CH_2)_n$ wherein $R_7$ is a saturated or unsaturated, branched or nonbranched alkyl with 7 to 21 carbon atoms and n has a typical value of 1-4; or (iii) has the structure $R_8COO(CH_2)_n$ wherein $R_8$ is a saturated or unsaturated, branched or nonbranched alkyl with 7 to 21 carbon atoms and n has a typical value of 1-4;
R4 (i) is H or a unsaturated or saturated, branched or nonbranched alkyl with 8 to 22 carbon atoms; (ii) has the structure $R_7CONH(CH_2)_n$, or (iii) has the structure $R_8COO(CH_2)_n$ wherein $R_7$ and $R_8$ and n are same as above;
$R_5$ and $R_6$ are individually hydrogen or an alkyl of an integer of 1 to 4 carbon atoms, and $X^-$ is an anion, for example a halide such as a chloride, sulfate or methosulfate.

Typical examples of compounds of structure I are cetyl trimethyl ammonium chloride, steardimonium chloride, dipalmitoyl dimonium chloride, distearyl dimethyl ammonium chloride, stearamidopropyl trimonium chloride, dioleoylethyl dimethyl ammonium methosulfate, and dioleoylethyl hydroxyethylmonium methosulfate. Other quaternary depositions aids include quaternium-8; quaternium-14; quaternium-15; quaternium-18; quaternium-22; quaternium-24; quaternium-26; quaternium-27; quaternium-30; quaternium-33; quaternium-37; quaternium-53; quaternium-60; quaternium-61; quaternium-72; quaternium-78; quaternium-80; quaternium-81; quaternium-82; quaternium-83; and quaternium-84.

Suitable cationic polymers are those having the INCI category name Polyquaternium. Typical examples are Polyquaternium-4, Polyquaternium-6, Polyquaternium-7, Polyquaternium-10, Polyquaternium-11, Polyquaternium-16, Polyquaternium-22, and Polyquaternium-28, with Polyquaternium 11 preferred (sold as Gafquat from ISP and as Luviquat PQ from BASF). Suitable cationic polymers to condition hair also include quaternized silicones such as silicone quaternium-3, silicone quaternium-4, and silicone quaternium-8. Silicones with aminofunctional groups such as amodimethicone are also suitable.

Amphoteric or zwitterionic compounds may also be used when the composition has a pH value that ensures a cationic character for the amphoteric or zwitterionic compound. Such materials are included in the definition of cationic deposition aid. Suitable polymeric materials are the copolymers of N-octylacrylamide, acrylic or methacrylic and tertbutylaminoethylmethacrylate known with its trade name Amphomer; and copolymers of methacryloylethylbetaine and alkyl methacrylate known as Yukaformer. Useful amphotheric or zwitterionic surfactants are in particular the various known betaines such as fatty acid amido alkyl heroines and sulfobetaines, for example, lauryl hydroxy sulfobetaines, long-chain alkylamino acids such as cocoaminoacetate, cocoaminopropionate and sodium cocoamphopionate and -acetate.

The cationic deposition aid is present in the hair coloring compositions of the invention in an amount of from about 0.05 to about 10% by weight, preferably 0.1 to 5% by weight, and more preferably about 2 to 4% by weight of the composition.

Vehicle

The composition can be aqueous or anhydrous. The composition can take various fluid forms, such as a suspension, dispersion, or emulsion. An emulsion can be of any conventional type, including oil-in-water, water-in-oil, silicone-in-water, water-in-silicone, wax-in-water, and water-in-wax. The wax based compositions can use a silicone wax material as the wax component. The composition typically exhibits the physical consistency of a lotion, cream, or gel, although pump sprays and aerosols may be suitable The compositions are preferably suspensions and water-in-silicone emulsions. When in an aqueous suspension, the composition is in a flowable form of shampoo-like consistency and when in the form of an emulsion, it has a cream consistency. The color will not water rinse off, but can be removed by washing with a shampoo.

The composition contains one or more cosmetically acceptable solvents in which the polymer is soluble or dispersible. Water is a preferred solvent in aqueous compositions. Other useful hydrophilic solvents include lower alcohols and polyhydric alcohols. Useful hydrophobic solvents include volatile and nonvolatile oils. The term "volatile" means the oil has a measurable vapor pressure, or a vapor pressure of at least 2 mm of mercury at 20° C. The term "nonvolatile" means that the oil has a vapor pressure of less than 2 mm of mercury at 20° C. Suitable volatile oils include linear silicones, for example low molecular weight dimethicones, cyclic silicones such as cylcomethicones, paraffinic hydrocarbons, or mixtures thereof. Straight or branched chain paraffinic hydrocarbons having 5 to 40 carbon atoms, more preferably 8 to 20 carbon atoms are suitable for use in the present invention, and may be volatile or nonvolatile depending on molecular weight and isomer form. Suitable nonvolatile oils include silicone oils, natural oils, and synthetic oils, including fatty esters and fatty alcohols. Among silicone oils are dimethicone, dimethiconol, polydimethylsiloxane, DC Fluids from Dow Corning; polysilicones, such as polysilicone-1, polysilicone-2, polyilicone-5, polysilicone-10, and polysilicone-14. Natural oils suitable herein are olive oil, almond oil, avocado oil, squalene, mineral oil, and combinations thereof. Suitable synthetic oils include the hydrogenated organic compounds, such as hydrogenated polydecene, hydrogenated rice bran oil, hydrogenated myristyl olive esters, and the like. Other oils are polyols such as glycerin, glycols, such as phytantriol, and low molecular weight polethylene glycols known with trade names Carbowax from Union. Other suitable nonvolatile oils include naturally occurring glyceryl esters of fatty acids or triglycerides. Suitable oils also include synthetic or semi-synthetic glyceryl esters, e.g. fatty acid mono-, di-, and triglycerides that have been modified. Modified glycerides include, for example, acetylated castor oil, glyceryl stearate, glyceryl dioleate, glyceryl distearate, glyceryl myristate, PEG castor oils, PEG glyceryl oleates, and PEG glyceryl stearates. Mention may also be made of include lanolin oil, triisocetyl citrate, $C_{10}$-$C_{18}$ triglycerides, coconut oil, corn oil, palm oil, and sunflower seed oil.

The solvent is present in an amount sufficient to dissolve or disperse the copolyol and other constituents, as well as otherwise provide a sufficient degree of fluidity to the composition. The concentration of the solvent depends on the form of the product composition, for example, a suspension versus an emulsion. Such concentration requirements are known to those of ordinary skill in the cosmetic arts. Typically, in the case of a suspension the solvent comprises the major portion of the composition and can be as high as 99% by weight of the composition, although more typically the solvent would comprise from about 65 to about 95% by weight of the composition, preferably from about 75 to 90% by weight. In the case of an emulsion the oil or silicone phase solvent together with the aqueous phase solvent comprises from about 10 to about 90%, more preferably present from about 25 to about 75%, and most preferably present from about 35 to about 65% by weight of the composition. In the specific case of the water-in-silicone emulsion form of the composition, which is preferred, the silicone phase comprises 10 to 50% by weight of the composition, preferably from about 20 to about 35%. Preferred as the silicone solvent is cyclomethicone and dimethicone, most preferably cyclomethicone. Water comprises up to 100% of the aqueous phase, more typically from about 85 to about 99%.

The compositions may also be in the form of a gel, the most typical gel system being one where gellant is mixed with a polyol or a nonvolatile oil such as a mineral oil or a hydrogenated polyisobutane. Suitable gellants include triblock polymers, but preferably are clays such as bentonites.

The compositions beneficially are thickened so that they do not run from the hair when applied to the hair. Suitable thickeners used in cosmetics include but are not limited to nonionic ethers such as hydroxyethyl and hydroxypropyl cellulose, a tetraester of stearic acid and polyethylene glycol ether of pentaerythritol with 100 to 200 moles of ethylene oxide such as PEG-150 pentaerythrityl tetrastearate sold under the trademark Crothix Liquid sold by Croda, PEG-150/decylalcohol/SMDI Copolymer, which is a copolymer of PEG-150, decyl alcohol and saturated methylene diphenyldiisocyanate monomers sold under the trademark Aculyn 44 by Rohm & Haas, PEG-75 Stearyl Ether Dimer IPDI, the reaction product of Steareth-75 and isophorone diisocyanate sold under the trademark Dermothix-75 sold by Amisol Company Ltd., and PEG-90M, which is a polymer of 90,000 moles of ethylene oxide sold under the trademark Polyox WSR-301 by Amerchol. The compositions may contain from about 0.1 to 15% by weight of a thickening agent.

Additional functional components may be incorporated in the compositions, in amounts effective to provide their functional benefits, as is known in the art.

Among the functional ingredients, mention may be made of emollients, conditioning agents, humectants, antidandruff agents, sunscreen agents and UV light absorbers, preservatives, fragrances, and dyes. Additionally, solubilizing agents, suspending agents, and stabilizers may be incorporated to ensure that the actives are maintained in solution or in stable emulsion.

Propellants may be incorporated in aerosol and mousse products. Suitable are hydrocarbon propellants and compressed gases.

The present invention can comprise sunscreens and/or UV filters present either for stabilization of the product color or for protection of hair from environment influences such as loss of elasticity, loss of hair color (bleaching effect of sun light). Suitable substances are: 4-Aminobenzoic acid and its esters and salts, cinnamic acid and the esters and salts thereof, 4-methoxycinnamic acid and the esters and salts thereof, salicylic acid and the esters and salts, 2,4-dihydroxybenzophenone.

In the following examples, there are described several preferred embodiments to illustrate the invention. However, it should be understood that the invention is not intended to be limited to the specific embodiments.

EXAMPLE 1

A hair dyeing composition was prepared comprising a suspension comprising 4.0% dimethiconol, 4.0% dicetyldimonium chloride, 0.05% PEG-90, 4% GE SF 1528 (a mixture of 92% cyclomethicone and 8% dimethicone copolyol), 0.20% imidazolidinyl urea, 0.50% Crothix Liquid (PEG-150 pentaerythrityl tetrastearate/C8-C10/Aqueous), 0.5% Aculyn 44 (PEG-150/decyl alcohol/SMDI copolymer (35% active aqueous solution), 1.0% hydroxyethyl cellulose HHR 250, 0.25% of cosmetic red oxide, 0.5% of iron oxide yellow, 0.5% of iron oxide black, and 84.5% of demineralized water.

Using the above-described composition, three separate tresses were treated to illustrate the ability of the composition to color hair. The procedure comprised treating a virgin, platinum blond, damp hair tress of about 4.20 g in weight with about 1 g of the composition for a minute with thumb and forefingers from the top of the tress to the bottom. The hair tress was rinsed for 15 to 20 seconds with water at 35 to 40° C. or until the rinse water ran clear. The hair tress was blow dried for about 1 minute until the hair was dry to the touch and then readings were taken with a Colortec-PCM hand held colorimeter and the readings were compared with an untreated control with respect to L*, a* and b* readings. The average results of 6 runs for each tress are reported in the following Table I.

TABLE I

|  | L* | a* | b* | ΔE* ab |
|---|---|---|---|---|
| Control | 70.07 | 9.71 | 23.58 |  |
| Tress 1 | 64.77 | 10.96 | 22.09 | 5.47 |
| Tress 2 | 64.13 | 11.37 | 22.07 | 6.19 |
| Tress 3 | 63.87 | 11.21 | 21.51 | 6.47 |

L* is a lightness scale from 100 (lightest or white) to 0 (darkest or black)
a* is a color scale from red to green compared to a standard sample with the higher the number being more red and the lower the number being more green.
b* is a color scale from yellow to blue with the higher the number being more yellow and the lower the number being more blue.
ΔE* ab is equal to the square root of $(\Delta L^*)^2 + (\Delta a^*)^2 + (\Delta b^*)^2$ which gives the color difference in a numerical value.

The test results confirm that the Tresses 1, 2, and 3 had color deposited on them, as indicated by the ΔE value.

EXAMPLE 2

A hair dyeing composition was prepared consisting of 15% by weight of GE SF 1528 (a mixture of 92% cyclomethicone and 8% dimethicone copolyol), 2% of sodium chloride, 0.2% of imidazolidinyl urea, 9% of cyclomethicone-pentamer, 1% cosmetic brown iron oxide, and 72.8% of demineralized water.

The procedure of Example 1 was repeated with the above-described composition and the results are reported in Table II

TABLE II

|  | L* | a* | b* | ΔE* ab |
|---|---|---|---|---|
| Control | 71.56 | 8.01 | 21.28 |  |
| Tress 1 | 68.20 | 11.85 | 22.06 | 5.16 |
| Tress 2 | 66.91 | 11.52 | 22.53 | 5.95 |
| Tress 3 | 68.09 | 11.11 | 22.07 | 4.72 |

The test results confirm that the Tresses 1, 2, and 3 had color deposited on them, as indicated by the ΔE value.

EXAMPLE 3

A hair dyeing composition was prepared containing 15% by weight of cyclomethicone/dimethicone copolyol 92/8, 2.0% by weight of sodium chloride, 0.20% of imidazolidinyl urea, 9.0% by weight of cyclomethicone-pentamer, 1.0% by weight of red iron oxide (Red Unispheres # P018.1935 available from Induchem), and 72.80% of demineralized water. A tress was dyed with this composition, warm water rinsed for 30 seconds, and then blow dried.

The composition of Example 3 was compared with two hair mascaras (Avon Color Trend Neon Shade Hair Mascara and Avon Color 2 Turquoise Shade Hair Mascara) for a color depositing treatment in which a tress of dry commercially bleached hair was treated with 1 gram of each composition, warm water rinsed for 30 seconds, and then blow dried. In a visual comparison, the tress treated with the composition of the invention was definitively more colored than the tresses treated with the hair mascara products.

EXAMPLE 4

A hair-dyeing composition was prepared containing 15.0% by weight of cyclomethicone/dimethicone copolyol 92/8, 2.0% by weight of sodium chloride, 0.2% by weight of imidazolidinyl urea, 9.0% by weight of cyclomethicone-pentamer, 2.67% by weight of microna-orange iron oxide (# 017499 available from EMD Chemicals), and 71.13% by weight of demineralized water.

The product of Example 4 was subjected to a color treatment rinse off test compared with a hair mascara (Avon Flame Red Hair Mascara) in which a commercially bleached hair tress was treated with 1 gram of each composition for one minute, rinsed with warm water, and blow dried. In a visual comparison, the composition of Example 4 clearly retained more color.

EXAMPLE 5

A hair dyeing composition was prepared containing 15.0% by weight of cyclomethicone/dimethicone copolyol, 2.0% of sodium chloride, 0.2% by weight of imidazolidinyl urea, 9.0% of cyclomethicone-pentamer, 0.375% by weight of Colorona sienna iron oxide# 107377, 1% microna-orange iron oxide (# 017499 from EMD Chemicals), and 72.425% by weight of demineralized water.

EXAMPLE 6

A hair dyeing composition was prepared comprising 15% by weight of cyclomethicone/dimethicone copolyol 92/8, 2.0% by weight of sodium chloride, 0.2% by weight of imidazolidinyl urea, 9.0% by weight of cyclomethicone-pentamer, 1.0% of dicetyldimonium chloride, 1.0% of ultramarine violet (cosmetic #3514 available from Sensient Technologies), and 71.80% of demineralized water.

Various modifications of the compositions and method of the invention may be made without departing from the spirit or scope thereof and it should be understood that the invention is intended to be limited only as defined in the appended claims.

What we claim is:

1. A method of dyeing hair on a person's head to impart a temporary hair coloring thereto comprising treating the hair with a temporary hair coloring composition comprising 0.1 to 15% of at least one inorganic colored pigment, 0.05 to 10% of a nonvolatile dimethicone copolyol having from 1 to about 30 moles ethylene oxide and from about 10 to about 50 moles propylene oxide, and water, and rinsing excess composition from the hair with water.

2. The method of claim 1 wherein the hair is first shampooed, the treatment is effected on the damp hair, and the hair is blow dried after the water rinse.

3. The method of claim 1 wherein the inorganic colored pigment is selected from the group consisting of iron oxide, chromium oxide green, ferric blue, carbon black, manganese violet, ultramarines, and combinations thereof.

4. The method of claim 3 wherein the inorganic colored pigment is selected from the group consisting of iron oxide, ultramarines, and combinations thereof.

5. The method of claim 4 wherein the inorganic colored pigment is an iron oxide selected from the group of red, yellow and black iron oxides.

6. The method of claim 1 wherein the dimethicone copolyol is present in the composition in an amount of from about 0.1 to 5%.

7. The method of claim 1 wherein the dimethicone copolyol has from 10 to 25 moles ethylene oxide and 15 to 30 moles propylene oxide.

8. The method of claim 7 wherein the dimethicone copolyol is selected from the group consisting of PEG/PPG-18/18 dimethicone, PEG/PPG-15/15 dimethicone, PEG/PPG-20/23 dimethicone, PEG/PPG-20/15 dimethicone, PEG-PPG-19/19 dimethicone, lauryl PEG/PPG-18/18 methicone, and mixtures thereof.

9. The method of claim 1 wherein the temporary hair coloring composition further comprises a cationic deposition aid present in an amount of from about 0.05 to 10%.

10. The method of claim 9 wherein the cationic deposition aid is selected from the group consisting of quaternary ammonium compounds and cationic polymers, the cationic deposition aid being present in an amount of from about 0.1 to 5%.

11. The method of claim 10 wherein the temporary hair coloring composition further comprises a volatile silicone, said composition being in the form of a water-in-silicone emulsion wherein the silicone phase comprises 10 to 50% by weight of the composition.

12. The method of claim 11 wherein the temporary hair coloring composition contains 1 to 5% iron oxide pigment and 0.05 to 2.5% dimethicone copolyol having 10 to 25 moles ethylene oxide and 15 to 25 moles propylene oxide.

13. The method of claim 10 wherein the temporary hair coloring composition is in the form of an aqueous suspension containing 1 to 5% iron oxide pigment and 0.05 to 2.5% dimethicone copolyol having 10 to 25 moles ethylene oxide and 15 to 25 moles propylene oxide.

14. The method of claim 1 wherein the temporary hair coloring composition is in the form of a water-in-silicone emulsion containing 1 to 5% iron oxide pigment and 0.05 to 2.5% dimethicone copolyol having 10 to 25 moles ethylene oxide and 15 to 25 moles propylene oxide, wherein the silicone phase comprises 10 to 50% by weight of the composition.

15. The method of claim 11 wherein the cationic deposition aid is a quaternary ammonium compound of the chemical formula

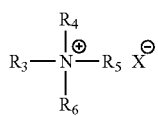

I wherein:
- $R_3$ (i) is a saturated or unsaturated, branched or nonbranched alkyl with 8 to 22 carbon atoms; (ii) has the structure $R_7CONH(CH_2)_n$ wherein $R_7$ is a saturated or unsaturated, branched or nonbranched alkyl with 7 to 21 carbon atoms and n has a typical value of 1-4; or (iii) has the structure $R_8COO(CH_2)_n$ wherein $R_8$ is a saturated or unsaturated, branched or nonbranched alkyl with 7 to 21 carbon atoms and n has a typical value of 1-4;
- $R_4$ (i) is H or a unsaturated or saturated, branched or nonbranched alkyl with 8 to 22 carbon atoms; (ii) has the structure $R_7CONH(CH_2)_n$, or (iii) has the structure $R_8COO(CH_2)_n$ wherein $R_7$ and $R_8$ and n are same as above;
- $R_5$ and $R_6$ are individually hydrogen or an alkyl of an integer of 1 to 4 carbon atoms, and X is an anion, for example a halide such as a chloride, sulfate or methosulfate.

16. The method of claim 7 wherein the inorganic colored pigment is selected from the group consisting of iron oxide, chromium oxide green, ferric blue, carbon black, manganese violet, ultramarines, and combinations thereof.

17. The method of claim 16 wherein the inorganic colored pigment is selected from the group consisting of iron oxide, ultramarines, and combinations thereof.

18. The method of claim 17 wherein the inorganic colored pigment is an iron oxide selected from the group of red, yellow and black iron oxides.

19. The method of claim 7 wherein the dimethicone copolyol is admixed with cyclomethicone, the weight ratio of the dimethicone copolyol to the cyclomethicone being from 95:5 to 5:95.

20. The method of claim 19 wherein the dimethicone copolyol is present in the composition in an amount of from about 0.1 to 5%.

21. The method of claim 7 wherein the temporary hair coloring composition is in the form of a water-in-silicone emulsion wherein the silicone phase comprises 10 to 50% by weight of the composition.

22. The method of claim 21 wherein the temporary hair coloring composition contains 1 to 5% iron oxide, and 0.05 to 10% cationic deposition aid.

23. The method of claim 1 wherein the temporary hair coloring composition is in the form of an aqueous suspension containing 1 to 5% iron oxide, 0.05 to 2.5% dimethicone copolyol having 10 to 25 moles ethylene oxide and 15 to 25 moles propylene oxide, and 0.05 to 10% cationic deposition aid.

24. The method of claim 1 wherein the temporary hair coloring composition is in the form of a water-in-silicone emulsion containing 1 to 5% iron oxide, 0.05 to 2.5% dimethicone copolyol having 10 to 25 moles ethylene oxide and 15 to 25 moles propylene oxide, and 0.05 to 10% cationic deposition aid, wherein the silicone phase comprises 10 to 50% by weight of the composition.

* * * * *